US00PP17145P2

(12) United States Plant Patent
Sanders

(10) Patent No.: US PP17,145 P2
(45) Date of Patent: Oct. 10, 2006

(54) **NEW GUINEA *IMPATIENS* PLANT NAMED 'INGSCAR'**

(50) Latin Name: *Impatiens hawkeri*
Varietal Denomination: Ingscar

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 35 days.

(21) Appl. No.: 11/222,555

(22) Filed: Sep. 9, 2005

(51) Int. Cl.
*A01H 5/00* (2006.01)

(52) U.S. Cl. ..... Plt./318
(58) Field of Classification Search ..... Plt./318
See application file for complete search history.

*Primary Examiner*—Kent Bell
*Assistant Examiner*—Annette H Para
(74) *Attorney, Agent, or Firm*—Bruce Vrana

(57) ABSTRACT

A new and distinct cultivar of New Guinea *Impatiens* plant named 'Ingscar' characterised by its large rounded red flowers, early flowering, dark green foliage, ball shaped growth habit with good basal branching and good outdoor vigor.

1 Drawing Sheet

Latin name of the genus and species of the plant claimed: *Impatiens hawkeri.*

Varietal denomination: 'Ingscar'.

BACKGROUND OF THE NEW PLANT

The present invention comprises a new and distinct New Guinea *Impatiens* plant botanically known as *Impatiens hawkeri* and referred to by the cultivar name 'Ingscar.'

The new cultivar was developed in a controlled breeding program conducted by the inventor in Enkhuizen, Netherlands. The new New Guinea *Impatiens* cultivar has an early flowering response, large flowers with attractive coloration and a good flowering behavior under field conditions.

The new cultivar is propagated from cuttings resulting from the cross in September 2001 of the proprietary New Guinea *Impatiens* selection identified as 'H294-2' as female parent and the proprietary New Guinea *Impatiens* selection identified as 'H288-1' as male parent. 'H294-2' and 'H288-1' are not commercially available and have not been patented.

As a result of this cross the present cultivar was selected in September 2002 in Enkhuizen, Netherlands and has been repeatedly asexually reproduced by cuttings in Enkhuizen, Netherlands, in Gilroy, Calif., and in Angers, France over a period of several years. The distinctive characteristics of this new *Impatiens* are stable and reproduced true to type in successive generations of asexual reproduction. It takes 9 to 11 weeks to produce a finished plant, starting from a rooted plug and planted in a 12 cm pot, depending on the temperature.

SUMMARY OF THE INVENTION

The following traits have been repeatedly observed and are determined to be the unique characteristics of 'Ingscar.' These characteristics in combination distinguish 'Ingscar' as a new and distinct New Guinea *Impatiens* cultivar:

1. Large rounded red flowers
2. Ball shaped growth habit with flowers on top of the foilage
3. Dark green foliage 4. Good basal branching character
5. Good outdoor vigor Plants of the new New Guinea *Impatient* differ primarily from the plants of the female parent selection in the following characteristic:

Plants of the New Guinea *Impatiens* have very large red flowers, whereas the plants of the female parent have large carmine red flowers.

Plants of the new New Guinea *Impatiens* differ primarily from the plants of the male parent selection in the following characteristic:

Plants of the New Guinea *Impatiens* have very large red flowers, whereas the plants of the male parent have large red flowers.

Plants of the new New Guinea *Impatiens* can be compared to plants of 'Moala,' U.S. Plant Pat. No. 10,301. In side-by-side comparisons conducted in Enkhuizen, Netherlands, plants of the new New Guinea *Impatiens* differed from plants of the cultivar 'Moala' in the following characteristics:

1. Plants of the new New Guinea *Impatiens* have very large flowers, whereas the plants of the cultivar 'Moala' have large flowers.
2. Plants of the new New Guinea *Impatiens* have a ball shaped growth habit, whereas plants of the cultivar 'Moala' have a bushy shaped growth habit.
3. Plants of the new New Guinea *Impatiens* have longer internodes and good plant vigor, whereas the cultivar 'Moala' have short internodes and moderate plant vigor.

DESCRIPTION OF THE DRAWING

This new New Guinea *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new New Guinea *Impatiens*. The data which defines these characteristics were collected from asexual reproductions carried out in Enkhuizen, Netherlands. The plant history was taken on 30 week old plants, blossomed under natural light in the field.

Color readings were taken in the laboratory under ambient light. Color references are primarily to The R.H.S. Color Chart of The Royal Horticultural Society of London.

The plant:
*Classification.*—Botantical: *Impatiens hawkeri.*
Parentage:
*Female parent.*—Proprietary *Impatiens hawkeri* selection identified as code number 'H294-2,' not patented.
*Male parent.*—Proprietary *Impatiens hawkeri* selection identified as Code number 'H288-1,' not patented.
Propagation:
*Type cutting.*—Terminal cuttings.
*Time to initiate roots.*—Approximately 7–14 days.
*Time to produce a rooted cutting.*—Approximately 21 days.
*Root description.*—Fine, fibrous, and white in color.
Plant description:
*General appearance.*—Outwardly spreading, low rounded and uniform mounded plant growth.
Habit:
*Growth and branching habit.*—Freely branching habit, freely flowering, vigorous.
Crop time:
*Plant height.*—25–29 cm.
*Plant spread.*—36–46 cm.
Lateral branch description:
*Length.*—24–27 cm.
*Diameter.*—4–7 mm.
*Texture.*—Smooth, glabrous.
*Internode length.*—0.6–7 cm.
*Color.*—RHS 187A.
Foliage description:
*Arrangement.*—Primarily in whorls.
*Length, mature leaves.*—8–9 cm.
*Width, mature leaves.*—3.5 cm.
*Shape.*—Lanceolate.
*Apex.*—Acute to acuminate.
*Base.*—Acute.
*Margin.*—Serrulate with fine cilation.
*Texture.*—Smooth, glabrous.
*Venation pattern.*—Pinnate.
*Color young foilage, upper surface.*—RHS 146A.
*Color young foliage, lower surface.*—RHS 146B and 174A.
*Fully expanded foliage, upper surface.*—RHS 147A.
*Fully expanded foliage, lower surface.*—RHS 146B.
*Venation, upper surface.*—RHS 42D.
*Venation, lower surface.*—RHS 185A.
*Petiole length.*—About 1.2 cm.
*Petiole diameter.*—About 5 mm.
*Texture.*—Smooth, glabrous.
*Color.*—RHS 185A.
Flower description:
*Flower type and flowering habit.*—Single.
*Number of flowers per leaf axil.*—1 or 2.
*Number of flowers and flower buds per lateral branch.*—6–7.
*Flower position.*—Above and beyond the foliage and typically facing upwards and outward.
*Flower shape.*—Rounded, mostly flat.
*Flowers lasting.*—About 10 days on the plant depending on environmental conditions.
*Petals.*—Self cleaning.
*Gynoecium.*—Persistent.
*Flowers.*—Not fragrant.
*Flowering.*—Indeterminate and continuous.
*Flowering season.*—Year round under greenhouse conditions. In the garden, flowering from spring until fall.
*Flower length.*—About 6.6–7 cm.
*Flower width.*—About 6.3–7 cm.
*Flower depth.*—About 0.2 cm.
Flower buds:
*Bud length.*—About 1.5 cm.
*Bud diameter.*—About 1.2 cm.
*Bud shape.*—Ovoid.
*Texture.*—Smooth, glabrous.
*Color, just before opening.*—RHS 46A.
Petals:
*Quantity.*—Single, five per flower, imbricate.
*Length of banner petal.*—About 3.1–3.3 cm.
*Width of banner petal.*—About 5–5.5 cm.
*Length lateral and basal petals.*—About 3.7–4.4 cm.
*Width lateral and basal petals.*—About 3.6–4.5 cm.
*Lateral and basal petal shape.*—Obcordate.
*Banner petal shape.*—Roughly obcordate.
*Petal apex.*—Retuse to emarginate.
*Petal base.*—Attenuate.
*Petal margin.*—Entire.
*Petal texture.*—Smooth, satiny.
*Petal color.*—Upper surface: When opening and fully opened: RHS 46B. Lower surface: When opening and fully opened: RHS 45C.
Spur:
*Length.*—About 5.7 cm.
*Texture.*—Smooth, glabrous.
*Aspect.*—Curved.
*Color.*—RHS 185A.
Peduncles:
*Length.*—About 5.7 cm.
*Strength.*—Strong, flexible.
*Diameter.*—0.2 mm.
*Aspect.*—About 45° from the stem.
*Color.*—RHS 185A.
Reproductive organs:
*Androecium.*—Stamen number: Five fused at anthers, filaments free, hooded.
*Anther shape.*—Obovate.
*Anther length.*—About 5 mm.
*Anther color.*—RHS 45C.
*Amount of pollen.*—Moderate.
*Pollen color.*—RHS 155B.
Gynoecium:
*Pistil number.*—One.
*Pistil length.*—About 6 mm.
*Stigma shape.*—Columnar, five segmented.
*Stigma color.*—Colorless.
*Style color.*—RHS 149D.
*Ovary arrangement.*—Five celled.
*Ovary color.*—RHS 144C.
*Seed development.*—Seed development has not been observed.
Disease and pest resistance: Resistance to pathogens and pests common to *Impatiens* has not been observed.

What is claimed is:

1. A new and distinct cultivar of New Guinea *Impatiens* plant named 'Ingscar', as substantially illustrated and described herein.

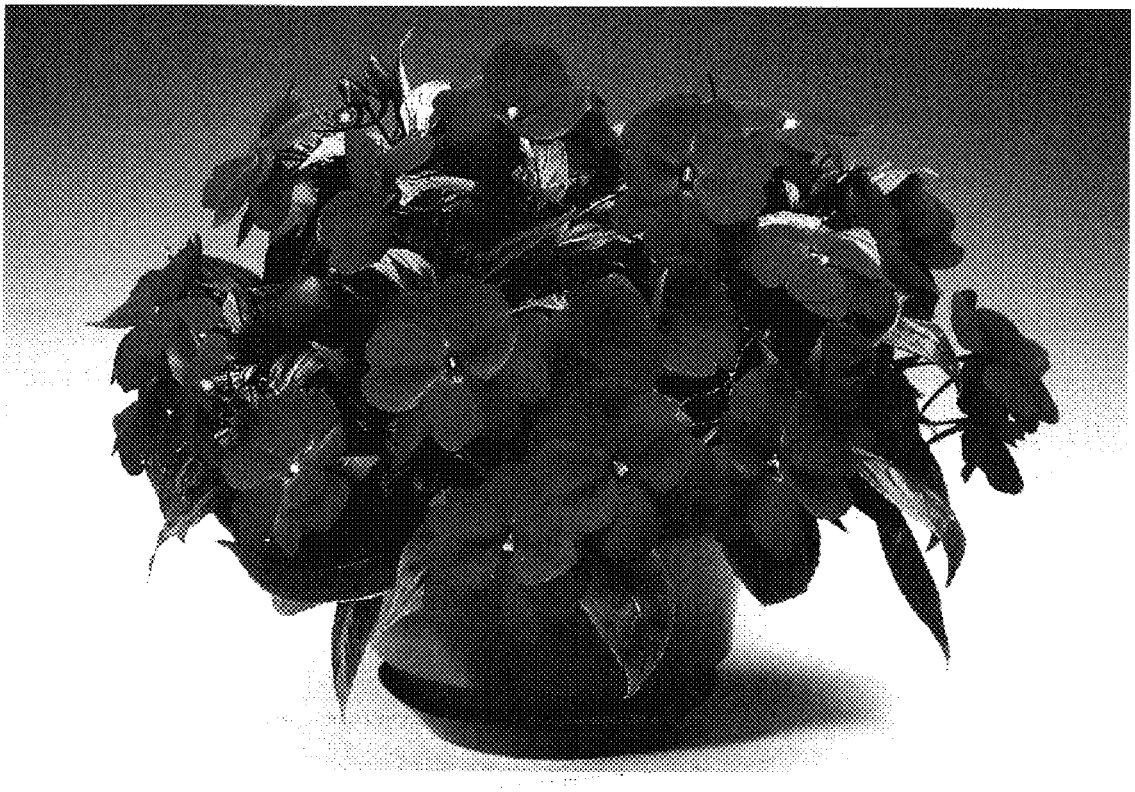

* * * * *